United States Patent
Roberts et al.

(10) Patent No.: US 7,992,569 B2
(45) Date of Patent: Aug. 9, 2011

(54) CUSTOMIZED TRANSITION ZONE SYSTEM AND METHOD FOR AN ABLATION PATTERN

(75) Inventors: Cynthia Roberts, Columbus, OH (US); Ashraf Mahmoud, New Albany, OH (US)

(73) Assignee: The Ohio State University, Columbus, OH (US)

( * ) Notice: Subject to any disclaimer, the term of this patent is extended or adjusted under 35 U.S.C. 154(b) by 1538 days.

(21) Appl. No.: 10/531,345

(22) PCT Filed: Oct. 15, 2003

(86) PCT No.: PCT/US03/32616
§ 371 (c)(1),
(2), (4) Date: Apr. 15, 2005

(87) PCT Pub. No.: WO2004/034928
PCT Pub. Date: Apr. 29, 2004

(65) Prior Publication Data
US 2006/0015090 A1    Jan. 19, 2006

(51) Int. Cl.
*A61B 19/00* (2006.01)
*A61B 18/18* (2006.01)
(52) U.S. Cl. ............................ 128/898; 606/5
(58) Field of Classification Search .............. 606/4, 5, 606/10–12, 18; 607/88, 89; 128/898
See application file for complete search history.

(56) References Cited

U.S. PATENT DOCUMENTS

| | | |
|---|---|---|
| 4,669,466 A | 6/1987 | L'Esperance |
| 4,721,379 A | 1/1988 | L'Esperance |
| 4,824,066 A | 4/1989 | Smith |
| 4,856,513 A | 8/1989 | Muller |
| 4,903,695 A | 2/1990 | Warner et al. |
| 4,941,093 A | 7/1990 | Marshall et al. |
| 5,098,426 A | 3/1992 | Sklar et al. |
| 5,613,965 A | 3/1997 | Muller |
| 5,891,131 A | 4/1999 | Rajan et al. |
| 5,935,140 A | 8/1999 | Buratto |
| 6,053,034 A | 4/2000 | Tsui et al. |
| 6,056,740 A | 5/2000 | Shimmick |
| 6,217,570 B1 | 4/2001 | Nevyas |
| 6,280,435 B1 | 8/2001 | Odrich et al. |
| 6,302,877 B1 | 10/2001 | Ruiz |
| 6,331,177 B1 | 12/2001 | Munnerlyn et al. |
| 6,530,917 B1 | 3/2003 | Seiler et al. |
| 6,547,393 B2 * | 4/2003 | Ruiz ............................. 351/212 |

(Continued)

FOREIGN PATENT DOCUMENTS

EP    1034756 A2    9/2003

(Continued)

OTHER PUBLICATIONS

Cynthia Roberts, PHD.; Corneal Biomechanics and Their Role in Corneal Ablative procedures; Chapter Nine; pp. 109-131.

(Continued)

*Primary Examiner* — Ahmed M Farah
(74) *Attorney, Agent, or Firm* — Dinsmore & Shohl, LLP

(57) ABSTRACT

The present invention discloses a corneal refractive procedure providing a customized transition zone. The customized transition zone provided according to the methods and systems of the present invention exhibits continuous curvature between an ablated optical zone and a non-ablated zone to address curvature discontinuity at the edge of the optical zone, thereby minimizing the biomechanical response and its postoperative effects on vision.

8 Claims, 13 Drawing Sheets

U.S. PATENT DOCUMENTS

| | | | |
|---|---|---|---|
| 6,582,078 | B2 | 6/2003 | Halpern et al. |
| 6,685,663 | B2 | 2/2004 | Feinsod |
| 2003/0208190 | A1* | 11/2003 | Roberts et al. .................... 606/5 |
| 2005/0096640 | A1 | 5/2005 | Dai et al. |
| 2005/0107775 | A1 | 5/2005 | Huang et al. |
| 2007/0073905 | A1 | 3/2007 | Roberts et al. |

FOREIGN PATENT DOCUMENTS

| | | |
|---|---|---|
| WO | 9111158 | 8/1991 |
| WO | 9316631 | 9/1993 |
| WO | 9418636 | 8/1994 |
| WO | 9853881 | 12/1998 |
| WO | 0128477 | 4/2001 |
| WO | 0128477 A1 | 4/2001 |
| WO | 0177739 | 10/2001 |
| WO | 0207660 A | 1/2002 |
| WO | 02069787 | 9/2002 |
| WO | 03082162 A2 | 10/2003 |
| WO | 2004034928 A2 | 4/2004 |
| WO | 2004058113 A1 | 7/2004 |

OTHER PUBLICATIONS

Office Action in U.S. Appl. No. 10/539,181, mailed Jul. 7, 2010 (8 pages).
Office Action in U.S. Appl. No. 10/332,891, mailed Apr. 28, 2010 (7 pages).
Office Action in U.S. Appl. No. 10/332,891, mailed Sep. 1, 2009 (5 pages).
Office Action in U.S. Appl. No. 10/332,891, mailed Mar. 17, 2009 (8 pages).
Office Action in U.S. Appl. No. 10/332,891, mailed Oct. 7, 2008 (5 pages).
Appeal Decision in U.S. Appl. No. 10/322,891, mailed Jul. 15, 2008 (22 pages).
Entry of Reply Brief in U.S. Appl. No. 10/332,891, mailed Sep. 7, 2007 (7 pages).
Examiner's Answer in U.S. Appl. No. 10/332,891, mailed Apr. 19, 2007 (10 pages).
Brief on Appeal in U.S. Appl. No. 10/332,891, filed Jan. 16, 2007 (35 pages).
Office Action in U.S. Appl. No. 10/332,891, mailed Aug. 17, 2006 (9 pages).
Office Action in U.S. Appl. No. 10/332,891, mailed Feb. 13, 2006 (8 pages).
Office Action in U.S. Appl. No. 10/332,891, mailed Aug. 24, 2005 (6 pages).
Office Action in U.S. Appl. No. 10/332,891, mailed Mar. 11, 2005 (6 pages).
Office Action in U.S. Appl. No. 10/332,891, mailed Jul. 14, 2004 (5 pages).
Examination Report in EP05013025.1, mailed Nov. 12, 2007 (4 pages).
Search Report in EP05013025.1, mailed Jul. 13, 2007 (3 pages).
Examination Report in EP01954818.9 mailed Jul. 3, 2003 (3 pages).
International Search Report in PCT/US2003/40302, mailed Jun. 14, 2004 (8 pages).
International Search Report in PCT/US2003/32616, mailed Apr. 15, 2004 (4 page).
International Search Report in PCT/US2001/22936, mailed Mar. 15, 2002 (4 pages).
International Preliminary Examination Report in PCT/US2001/22936, mailed Jun. 17, 2002 (3 pages).
Office Action in CA2416598, mailed Apr. 29, 2010 (3 pages).
Office Action in CA2416598, mailed May 14, 2009 (2 pages).
Office Action in CA2416598, mailed Dec. 12, 2007 (4 pages).
Office Action in CA2416598, mailed Nov. 29, 2006 (4 pages).
Examination Report in EP05013025.1, mailed Apr. 1, 2008 (3 pages).
Examination Report in EP03808464.6, mailed Dec. 12, 2008 (4 pages).
Office Action in JP2004563726 (translation), mailed Feb. 9, 2010 (8 pages).

Office Action in JP2004563726 (translation), mailed Aug. 14, 2009 (5 pages).
Office Action in CN200380106306.5 (translation), mailed Oct. 17, 2008 (3 pages).
Office Action in CN200380106306.5 (translation), mailed Apr. 20, 2007 (3 pages).
Office Action in CN200380106306.5 (translation), mailed Aug. 11, 2006 (5 pages).
Examination Report in SG200301781 1, mailed Oct. 11, 2006 (4 pages).
Search Report and Opinion in SG20030178 1, mailed Feb. 8, 2006 (8 pages).
Examination Report in EP01954818.9, mailed Feb. 17, 2005 (2 pages).
Examination Report in EP03808464.6, mailed Feb. 1, 2010 (3 pages).
Examination Report in AU2003303332, mailed Jul. 2, 2009 (2 pages).
Examination Report in AU2003303332, mailed Mar. 25, 2008 (3 pages).
Anseth A et al., Polysaccharides in normal and pathologic corneas, Invest Ophthalmol Vis Sci 1962; 1:195-201.
Applegate RA et al., Corneal abberations, visual performance after radial keratectomy, Journal of Refractive Surgery, 14: 397-407, 1998.
Applegate RA et al., Refractive surgery, optical abberations, and visual performance, Journal of Refractive Surgery, 13: 295-299, 1997.
Choi Yi et al., Corneal flap dimensions in laser in situ keratomileusis using the Innovatome automatic microkeratome, 14 Korean J. Ophthalmol. 7-11 (2000). (Abstract).
Chongsiriwatana et al., Correction of surface tilt in intra-operative corneal topography, poster (1998).
Dupps WJ et al., Geometric bias in PTK ablation profiles and associated keratometric changes in human globes, Investigative Ophthalmology and Visual Science Suppl, 1996, 37(3):S57.
Dupps WJ et al., Peripheral lamellar relaxation: a mechanism of induced corneal flattening in PTK and PRK? Investigative Ophthalmology and Visual Science Suppl, 1995, 36(4):S708.
Dupps WJ et al., Suppression of the acute biomechanical response to excimer laser keratectomy, Investigative Ophthalmology and Visual Science Suppl, 1999, 40(4):S110.
Hanna KD et al., Computer simulation of arcuate keratotomy for astigmatism, Refractive & Corneal Surgery, vol. 8, 1992, p. 152-163.
Katsube et al., A constitutive theory for porous composite materials, International Journal of Solids and Structures, vol. 35, pp. 4587-4596 (1998).
Katsube et al., The modified mixture theory for fluid-filled porous materials: theory, Journal of Applied Mechanics, Mar. 1987, vol. 54, pp. 35-40.
Katsube, The constitutive theory for fluid-filled porous materials, Journal of Applied Mechanics; 1985; 52: 185-189.
Komai Y et al., The three-dimensional organization of collagen fibrils in the human cornea and sclera, Invest Ophthalmol Vis Sci. 1991; 32: 2244-2258.
Munnerlyn CR et al., Photorefractive keratectomy: a technique for laser refractive surgery, J Cataract Refract Surg. 1988; 14: 46-52.
Oshika T et al., Comparison of corneal wavefront aberrations after photorefractive keratectomy and laser in situ keratomileusis, American Journal of Ophthalmology, 127: 1-7, 1999.
Pinsky PM et al., A microstructurally-based finite element model of the incised human cornea, J Biomech 1991; 24: 907-922.
Pinsky PM et al., Numerical modeling of radial, astigmatic, and hexagonal keratotomy, Refract Corneal Surg 1992: 8: 164-172.
Roberts C et al., Poster presentation "Characterization of corneal curvature changes inside and outside the ablation zone in LASIK," May 3, 2000.
Roberts C, [Abstract] Characterization of corneal curvature changes inside and outside the ablation zone in LASIK, Investigative Ophthalmology and Visual Science Suppl, Mar. 15, 2000; 41(4): S679.
Roberts et al., "The role of corneal biomechanics in customized ablative procedures," In MacRae S., Krueger R., Applegate R (eds). Customized Corneal Ablation, Thorofare, NJ; SLACK Incorporated, 2001.

Roy P et al., Computational models of the effects of hydration on corneal biomechanics and the results of radial keratotomy, Journal of Biomechanical Engineering, Transactions of the ASME, vol. 118, 1996, p. 255-258.

Smolek MK et al., Interlamellar adhesive strength in human eye bank corneas, Invest Ophthalmol Vis Sci., 1990; 31: 1087-1095.

Smolek MK, Interlamellar cohesive strength in the vertical meridian of human eye bank corneas, Invest Ophthalmol Vis Sci., 1993; 34: 2962-2969.

Velinsky SA et al., On the computer-aided and optimal design of keratorefractive surgery, Refract Corneal Surg 1992; 8:173-182.

Veress AI et al., Biomechanical response of the corneal to photorefractive keratectomy, Investigative Ophthalmology and Visual Science Suppl, 1995; 36(4): S705.

Vito RP et al., A mechanical model of the cornea: the effects of physiological and surgical factors on radial keratotomy surgery, Refractive & Corneal Surgery, 1989, p. 82-88.

Von Kulajta et al., Posterior corneal astigmatism in a refractive surgery population poster (1999).

U.S. Appl. No. 10/539,181—Office Action mailed Mar. 7, 2011 (9 pages).

Amm M et al., Refractive changes after phototherapeutic keratectomy, J Cataract Refract Surg. 1997; 23:839-844.

Biswell R, Cornea in: Vaughn DG, Asbury T, Riordan-Eva P, eds. General Ophthalmology. Norwalk, CT: Appleton & Lange, 1992: 125.

Bogan SJ et al., Classification of normal corneal topography based on computer-assisted videokeratography, Archives of Ophthalmology, 108(7):945-9, 1990.

Bryant MR et al., Finite element analysis of corneal topographic changes after excimer laser phototherapeutic keratectomy, Invest Ophthalmol Vis Sci 1993; 31 (suppl):804.

Bryant MR et al., Mathematical models of picosecond laser keratomileusis for high myopia, Journal of Refractive Surgery, vol. 16, 2000, p. 155-162.

Campos M et al., Clinical follow-up of phototherapeutic keratectomy for treatment of corneal opacities, Am J Ophthalmol. 1993; 115:433-440.

Dupps WJ, Chemo-mechanical modification of the corneal response to photokeratectomy [dissertation]. Columbus (OH): The Ohio State University, 1998.

Dupps WJ, Peripheral stromal expansion and anterior corneal flattening in phototherapeutic keratectomy: an in vitro human study [thesis], Columbus (OH): The Ohio State University, 1995.

Ehlers N, Studies on the hydration of the cornea with special reference to the acid hydration, Acta Ophthalmol. 1966; 44:924-925.

Ehlers N, The fibrillary texture and the hydration of the cornea, Acta Ophthalmol 1966; 44:620-630.

Fagerholm P et al., Phototherapeutic keratectomy: long-term results in 166 eyes, Refract Corneal Surg. 1993; 9(suppl): S76-81.

Fand AK, Effects of phototherapeutic keratectomy on perifpheral corneal thickness [ARVO Abstract], Invest Ophthalmol Vis Sci.1996; 37(3):S568 nr 2609.

Gartry D et al., Excimer laser treatment of corneal surface pathology: a laboratory and clinical study, Br J Ophthalmol. 1991; 75:258-269.

Gilbert ML et al., Corneal flattening by shallow circular trephination in human eye bank eyes, Refract Corneal Surg 1990; 6:113-116.

Gilbert ML et al., Human corneal steepening by annular keratotomy, Invest Ophthalmol Vis Sci1989; 30(suppl):186.

Hahn TW et al., Phototherapeutic keratectomy in 9 eyes with superficial corneal diseases, Refract Corneal Surg. 1993; 9(suppl): S115-118.

Hanna KD et al., Preliminary computer simulation of the effects of radial keratotomy, Arch Ophthalmol 1989; 107:911-918.

Hedbys BO et al., A new method for the determination of the swelling pressure of the corneal stroma in vitro, Exp Eye Res 1963; 2:122-129.

Hedbys BO et al., Flow of water in the corneal stroma, Exp Eye Res 1962; 1:262-275.

Hedbys BO et al., The imbibation pressure of the corneal stroma, Exp Eye Res 1963; 2:99-111.

Hee MR et al., Quantitative assessment of macular edema with optical coherence tomography, Arch Ophthalmology 1995; 113: 1019-1029.

Hee MR et al., Optical coherence tomography for ophthalmic imaging, IEEE Engineering in Medicine and Biiology 1995; 14: 67-76.

Hee MR et al., Topography of diabetic macular edema with optical coherence tomography, Ophthalmology, 1998, vol. 15, 2: 360-370.

Hersh PS et al., Phototherapeutic keratectomy: strategies and results in 12 eyes, Refract Corneal Surg. 1993; 9 (suppl):S90-95.

Hjortdal JO, Region elastic performance of the human cornea, Journal of Biomechanics (1996) 29, 931-942.

Huang D et al., Optical coherence tomography, Science 1991; 254: 1178-1181.

Izatt, J et al., Micrometer-Scale Resolution Imgaing of the Anterior Eye in Vivo with Optical Coherence Tomography, Arch Opthalmol, vol. 112, Dec. 1994 (6 pages).

Jakus MA, The fine structure of the human cornea, In: Smelser GK, ed, The Structure of the Eye, New York, NY: Academic Press, 1961.

Jue B, et al., The mechanical properties of the rabbit and human cornea, J Biomechanics 1986; 19:847-853.

Kanai A et al., Electron microscopic studies of swollen corneal stroma, Ann Ophthalmol 1973; 5:178-190.

Klyce SD et al., In vivo determination or corneal swelling pressure, Exp EyeRes 1971; 11:220-229.

Koers DM, The measurement of human corneal thickness by photography [master's thesis]. Columbus, OH: The Ohio State University; 1982.

Lembach, poster presentation, The Refractive Effect of the Flap in Laser in situ keratomileusis (LASIK), 2001.

Lindstrom RL et al., Six-month results of hyperopic and stigmatic LASIK in eyes with primary and secondary hyperopia, Tr AM Ophth Soc 1999, XCVII:241-260.

Litwin KL et al., Changes in corneal curvature at different excimer laser ablative depths, Am J Ophthalmol. 1991; 111:382-384.

MacRae SM et al., Large optical zone ablation treatment of myopia in the Oregon-Kansas study, Investigative Ophthalmology and Visual Sciences Suppl. 1999; 40(4):S588. [Abstract #3087].

Mahmoud AM et al., poster presentation, The Ohio State University Corneal Topography Tool. Abstract, Invest Ophthalmol Vis Sci 2000; 41:S677.

Maloney RK, A prototype erodible mask delivery system for the excimer laser, Ophthalmology 1993; 100:542-549.

Marshall J et al., An untrastructural study of corneal incisions induced by an excimer laser at 193 nm, Ophthalmol 1985; 92:749-758.

Maurice DM et al, Cohesive strength of corneal lamellae, Exp Eye Res 1990; 50:59-63.

Maurice DM, The cornea and sclera. In: Dayson H, ed, The eye. vol. lb: vegetative physiology and biochemistry. Orlando, FL: Academic Press, 1984:1-158.

Maurice DM, The movement of fluorescein and water in the cornea, Am J Ophthalmol 1960; 49:1011-1019.

McDonnell PJ et al., Phototherapeutic keratectomy with excimer laser for Reis-Buckler's corneal dystrophy, Refract Corneal Surg. 1992; 8:306-310.

Mishima S et al., The effect of normal evaporation on the eye, Exp Eye Res 1961; 1:46-52.

Mishima S et al., The permeability of the corneal epithelium and endothelium to water, Exp Eye Res 1967; 6:10-32.

O'Brart DPS et al., Treatment of band keratopathy by excimer laser phototherapeutic keratectomy: surgical techniques and long term follow up, Br J Ophthalmol. 1993; 77:702-708.

Örndahl M et al., Treatment of corneal dystrophies with excimer laser, Acta Ophthalmol. 1994; 72:235-240.

Pinsky PM et al., A microstructurally-based mechanical model of the human cornea with application to keratotomy, Invest Ophthalmol Vis Sci 1994; 31 (suppl): 1296.

Polack FM, Morphology of the cornea, I: study with silver stains, Am J Ophthalmol. 1961; 51:179.

Reinstein DZ et al., Very high-frequency ultrasound corneal analysis identifies anatomic correlates of optical complications of lamellar refractive surgery: anatomic diagnosis in lamellar surgery, Ophthalmology, 1999, 106(3): 474-82.

Reinstein DZ et al., Arc-scanning very high-frequency digital ultrasound for 3D pachymetric mapping of the corneal epithelium and stroma in laser in situ keratomileusis, Journal of Refractive Surgery, vol. 16, Jul./Aug. 2000 (pp. 414-430).

Roberts, The cornea is not a piece of plastic, editorial, Journal of Refractive Surgery, vol. 16, Jul./Aug. 2000.

Rogers et al., Phototherapeutic keratectomy for Reis Bucklers' corneal dystrophy, Austral N Zealand J Ophthalmol. 1993; 21:247-250.

Seiler TS et al., Does Bowman's layer determine the biomechanical properties of the cornea? Refract Corneal Surg1992; 8:139-142.

Sher NA et al., Clinical use of the 193-nm excimer laser in the treatment of corneal scars, Arch Ophthalmol. 1991; 109:491-498.

Shin TJ et al., The distribution of strain in the human cornea (1997) 30, 497-503.

Spoerl E, The swelling behaviour of the cornea after artificial cross-linking. ARVO abstracts, Invest Ophthalmol Vis Sci1997; 38:S507.

Stark W et al., Clinical follow-up of 193-nm ArF excimer laser photokeratectomy, Ophthalmol. 1992; 99:805-812.

Starr MS et al., Excimer laser phototherapeutic keratectomy, Cornea 1996; 15:557-565.

Thompson VM, Excimer laser phototherapeutic keratectomy: clinical and surgical aspects, Ophthalmic Surg & Lasers 1995; 26:461-472.

Waring GO III, Corneal structure and pathophysiology. In: Leibowits HM, ed. Corneal disorders: clinical diagnosis and management, Philadephia, PA: WB Saunders, 1984:3-25.

Ytteborg J et al., Corneal edema and intraocular pressure II Clinical results, Arch Ophthalmol 1965; 74:375-381.

Dierick HG et al., Is the corneal contour influenced by a tension in the superficial epithelial cells? A new hypothesis, Refract Corneal Surg 1992; 8:54-59, Comments in: Refract Corneal Surg 1992; 8:60 and 1993; 9:147.

McDonald MB et al., "Autonomous custom cornea LASIK," First International Congress of Wavefront Sensing and Aberration Free Ablative Corrections, Optical Society of America Annual Meeting, 2000 (Non-archived Presentation; partial summary of presented material provided).

Munger R et al., "Ablation profile and epithelial regrowth after myopic PRK with VISX Star," American Society of Cataract and Refractive Surgery Annual Meeting, 1999 (Non-archived Presentation; partial summary of presented material provided).

Roberts, "Customization and Corneal Response," Bausch & Lomb Refractive Alliance, held in conjunction with the American Academy of Ophthalmology, Dallas, Texas, Oct. 22, 2000.

Sborgia et al., "Corneal interactived programmed topographic ablation: preliminary results," American Society of Cataract and Refractive Surgery Annual Meeting, 1999 (Non-archived Presentation; partial summary of presented material provided).

Seiler T, "Der excimer-laser: ein instrument fur die hornhautchirurgie," Der Ophthalmologe. 1992; 89:128-133 (Reference not available; partial summary of material therein provided).

* cited by examiner

CUSTOMIZED TRANSITION ZONE SYSTEM AND METHOD FOR AN ABLATION PATTERN

The present invention relates generally to eye surgery, and more particularly to a corneal refractive procedure providing a customized transition zone, which exhibits continuous curvature between an ablated optical zone and a non-ablated zone to address curvature discontinuity at the edge of the optical zone, thereby minimizing the biomechanical response and its post-operative effects on vision.

Approximately 60% of Americans have refractive errors, and millions of people are myopic worldwide. Thousands of laser refractive surgeries are performed every year for the correction of myopia. Of the many individuals treated, about 15% to 50% do not achieve 20/20 vision due, at least in part, to the relationship of the patient eye to the mean population response eye, the dependence of refractive procedures on the mean population response eye, and ablation patterns that do not take advantage of the widest possible ablation zone achievable biomechanically. Additionally, many individuals cannot benefit from conventional corneal ablative techniques because their eyes do not fall within parameters modeled by the mean population response eye. For example, using conventional techniques, some corneas are not thick enough for a desired correction.

Early attempts at photorefractive keratectomy (PRK) modeled the cornea as two refracting surfaces with a bulk material in between the two refracting surfaces where there was a known index of refraction. In treating myopia, the goal was to increase the anterior radius of curvature, thus decreasing the curvature of the anterior surface. A simple geometric formula resulted, which assumes that the targeted corneal shape was a function of the ablation profile. This is the "shape subtraction" paradigm which assumes that the final corneal shape is determined by how much tissue is subtracted (ablated) by a laser. Essentially, this model treats the cornea as a piece of plastic to be sculpted into an ideal surface shape by laser ablation.

For example, FIG. 1 is a schematic of the simple "shape-subtraction" paradigm for correcting myopia where the cornea is initially "too curved" and thus is conventionally "reshaped" towards a desired "flatter" profile. $R_1$ and $R_2$ are initial and final radii of curvature, respectively, d is the maximum ablation depth, and S is the diameter of the optical zone. In some conventional processes, the starting point in determining how much material is to be removed from the center of the cornea to change its curvature is determined by the following geometric formula, the Munnerlyn formula: $d=R_2-\sqrt{R_1^2-h^2}-R_2+\sqrt{R_2^2-h^2}$, where $R_1-\sqrt{R_1^2-h^2}$ is the distance of center front from origin, and R2 is the new desired radius of curvature. In other conventional processes, the starting point within the optical zone is an approximation of the Munnerlyn formula, which says that $d=DS^2/3$ where D is the amount of desired diopter treatment and S is the optical zone, which is equal to 2 h. As typically used, this approximation calls for a 12-micron depth ablation of corneal tissue per diopter of treatment over a 6.0 mm chord treatment zone.

FIG. 2 is another schematic diagram of the shape-subtraction model of refractive surgery for a myopic ablation. The pre-operative radius of curvature is $R_1$ and the desired post-operative curvature is $R_2$. The intervening tissue between the pre-operative curve (solid) and post-operative curve (dashed) is "subtracted" with an excimer laser to produce the desired result. Thus, conventionally, corrections are limited by the amount and/or character of ablation that can occur within the optical zone. The shape subtraction model assumes that the only portion of the cornea that is changed during an ablative procedure is the area within the ablation zone and that even if there are changes outside the ablation zone; they have no effect on central vision. Thus, ablation patterns conventionally do not account for the corrective effect outside the optical zone caused by the biomechanical response of the cornea to the operative procedure. While the shape subtraction model has yielded satisfactory results without considering the biomechanical response of the cornea to perturbation, it can be improved.

Additionally, the conventional reshaping in the conventional optical zone of a cornea has unanticipated and undesired results. By way of illustration shown in FIG. 3, the edge of optical zone S where the ablated cornea meets the non-ablated cornea is a both a slope and a curvature discontinuity (i.e., points where the first and second derivatives along a programmed contour are step functions), which results in various visual problems including, but not limited to, spherical aberration, glare and halo effects. These effects can be particularly acute in low light conditions when the pupil enlarges. It is to be appreciated that the larger the difference between $R_1$ and $R_2$, the greater the slop and curvature discontinuities.

Conventionally, a transition zone is added to ablation patterns used in regular procedures and "customized" procedures (e.g., those based on topographical and/or wave-front analyses). As shown by FIG. 4, the transition zone is defined as the area between programmed optical zone $S_1$ and the ablation zone $S_2$ used for the corrective procedure. For example, a one or two millimeter wide transition zone is added to a conventional (e.g., six millimeter) optical zone for a total ablation pattern of around eight millimeters.

Conventional transition zones are typically linear or stepwise reduction patterns sized to be completed in the allocated transition zone width. Although such conventional transition zones reduce the abrupt change in slope between the "programmed" optical zone (i.e., area of cornea ablated for corrected measures) and non-ablated cornea in an attempt to minimize the above-mentioned visual problems, they are not thought to contribute to the corrective effect and improved image quality anticipated by ablation in the optical zone. Additionally, such conventional transition zones still have a curvature discontinuity and high curvature that generates a spherical aberration. Furthermore, the corrective effect of the transition zone on vision is not conventionally accounted for in conventional or customized procedures. Moreover, both regular conventional procedures and customized conventional procedures are limited by the amount of available cornea to ablate. Conventionally, the wider the optical zone is made, the deeper is the depth of ablation. Understandably, there is a finite amount of corneal depth to ablate, and thus, with conventional patterns, a finite ablatable width. For example, FIG. 5 illustrates two sample depths for two sample optical zone widths. To illustrate, for a desired ten or twelve diopter myopic correction, with a 500 micron thick cornea, conventional patterns may be limited to a 4.5 mm optical zone before running out of ablatable cornea. For a desired correction, 4.5 mm may not be wide enough even with a 1.5 mm conventional transition zone, and induce glare, and/or halos and/or spherical aberration. Thus, conventional methods may not produce the desired correction.

Accordingly, there is room for more improvement based on the methods and systems described herein.

In one embodiment, a corneal ablative pattern based on individual biomechanical responses to cutting, ablating and/or peeling a cornea is disclosed. The corneal ablative pattern includes a wider correction zone that includes both an optical zone and a transition zone, where the transition zone has a continuous curvature and its effects on vision correction are accounted for in the pattern design. The individual biomechanical responses can be predicted from pre-operative measurements and/or from measurements taken during surgery such as for example, after a flap cut during laser in-situ keratomileusis (LASIK). The individual biomechanical responses can depend on significant differences in the material properties of living human corneas and thus, there are significant differences in the responses of various individuals to similar ablative profiles.

Since a flap is cut in a LASIK procedure, the biomechanical responses of the cornea to the cut can be employed to predict a biomechanical response to ablation. Thus, measurements taken before and after cutting the flap facilitate adapting parameters for subsequent ablative steps. The prediction can be facilitated by reference to a biomechanical response model that relates inputs to outputs in light of a plurality of relationships between corneal measurements and individual responses that lead to post ablative corneal shape. In procedures like those where no flap is cut, such as for example, LASEK and PRK, predictions about biomechanical responses can still be made based on pre-operative measurements and a biomechanical response model. In another embodiment, a method for improving a transition zone is disclosed. The method comprises measuring a peripheral curvature of a pre-operative cornea, and developing an ablation depth profile in a transition zone, where the ablation depth profile will produce a continuous curvature on the surface of a post-operative cornea, where the curvature will be continuous through the transition zone.

In still another embodiment, a system for customizing an ablative pattern design with an improved ablation zone comprising both an ablated optical zone and an ablated transitional zone of continuous curvature is disclosed. The system comprises means for acquiring a pre-operative data by measuring a cornea pre-operatively, and means for acquiring a post-perturbation data by measuring a cornea after a perturbation has been applied to the cornea. The system further includes means for acquiring a prediction data of the biomechanical response of a cornea to ablation based, at least in part, on the pre-operative data and the post-perturbation data, and means for designing an ablation pattern based, at least in part, on the prediction data, where the ablation pattern considers the corrective effect of a transition zone.

In still another embodiment a method for customizing a transition zone for a refractive ophthalmic treatment is disclosed. The method comprises measuring a curvature of a pre-operative cornea. The method further includes developing an ablation depth profile in a transition zone, where the ablation depth profile will produce a continuous curvature on the surface of a post-operative cornea, where the curvature will be continuous throughout the transition zone thereby minimizing curvature discontinuities.

In yet another embodiment, a system for customizing a transition zone of an ablation pattern for a refractive ophthalmic treatment for a cornea is disclosed. The system comprises a data receiver for receiving a corneal data. The system further includes a transition zone designer adapted to produce the customized transition zone with a continuous curvature which eliminates curvature discontinuities at or near the edge of a post-operative optical zone and whose effects minimizes the biomechanical response in the post-operative cornea.

In another embodiment, a method to facilitate an increased functional optical zone with a customized transition zone pattern of continuous curvature, where the corrective properties of the transition zone are included in the ablation zone pattern design is disclosed. The method comprises receiving pre-operative data concerning a cornea on which a refractive ophthalmic treatment will be performed, and subtracting the programmed optical zone correction from corneal measurements provided in the pre-operative data to provide location of the programmed optical zone edge. The method further includes calculating the predicted curvature at and/or near the edge of the optical zone after application of the programmed optical zone correction, and calculating based, at least in part, on the pre-operative data received and the predicted curvature at the edge, a customized transition zone pattern. The customized transition zone addresses curvature discontinuity by eliminating its occurrence in and/or near the programmed optical zone. The method also includes applying the calculated transition zone to the ablation zone pattern.

These and other features and advantages of the invention will be more fully understood from the following description of preferred embodiments of the invention taken together with the accompanying drawings. It is noted that the scope of the claims is defined by the recitations therein and not by the specific discussion of features and advantages set forth in the present description.

The following detailed description of the embodiments of the present invention can be best understood when read in conjunction with the following drawings, where like structure is indicated with like reference numerals and in which.

Figure 1:
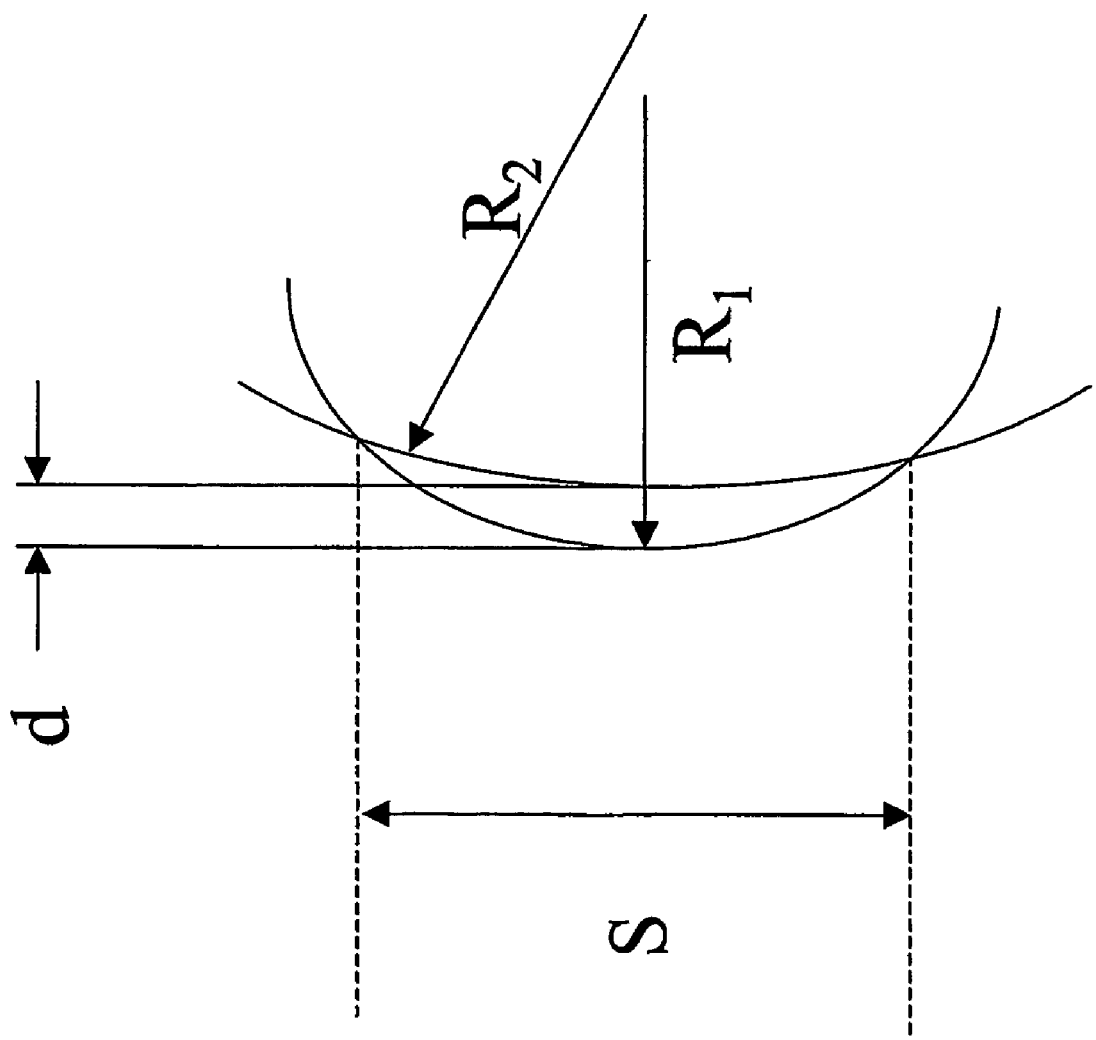
FIG. 1 illustrates a shape subtraction model.
Figure 2:
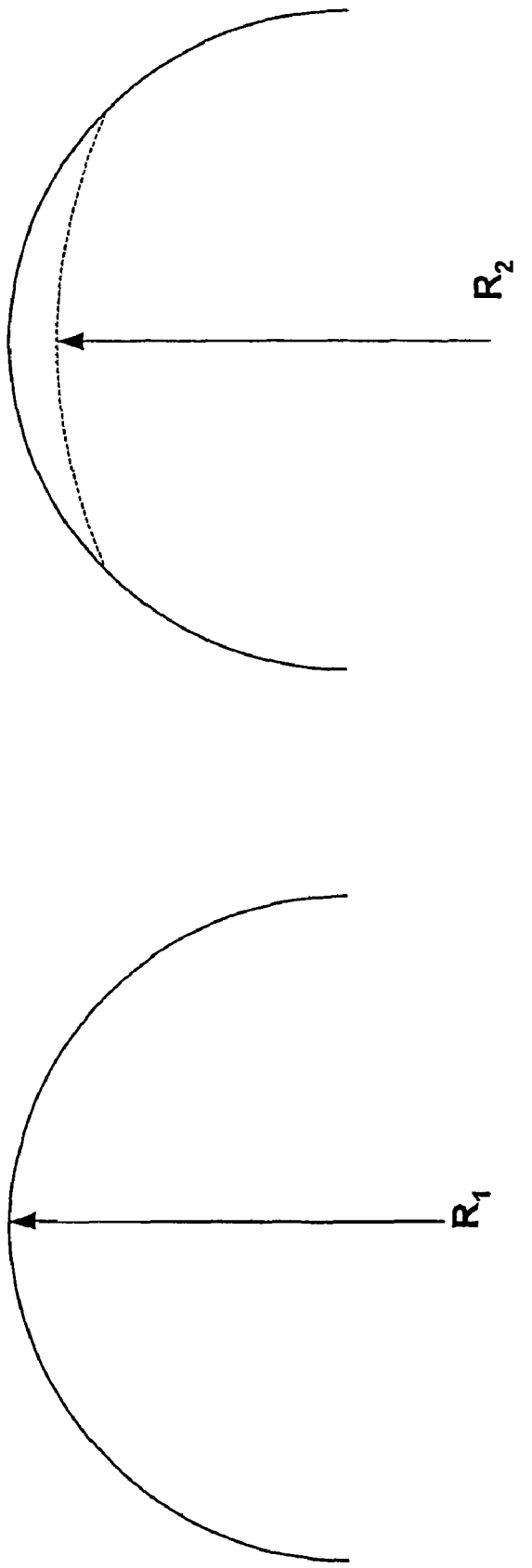
FIG. 2 illustrates a shape subtraction model of refractive surgery for myopic ablation.
Figure 3:
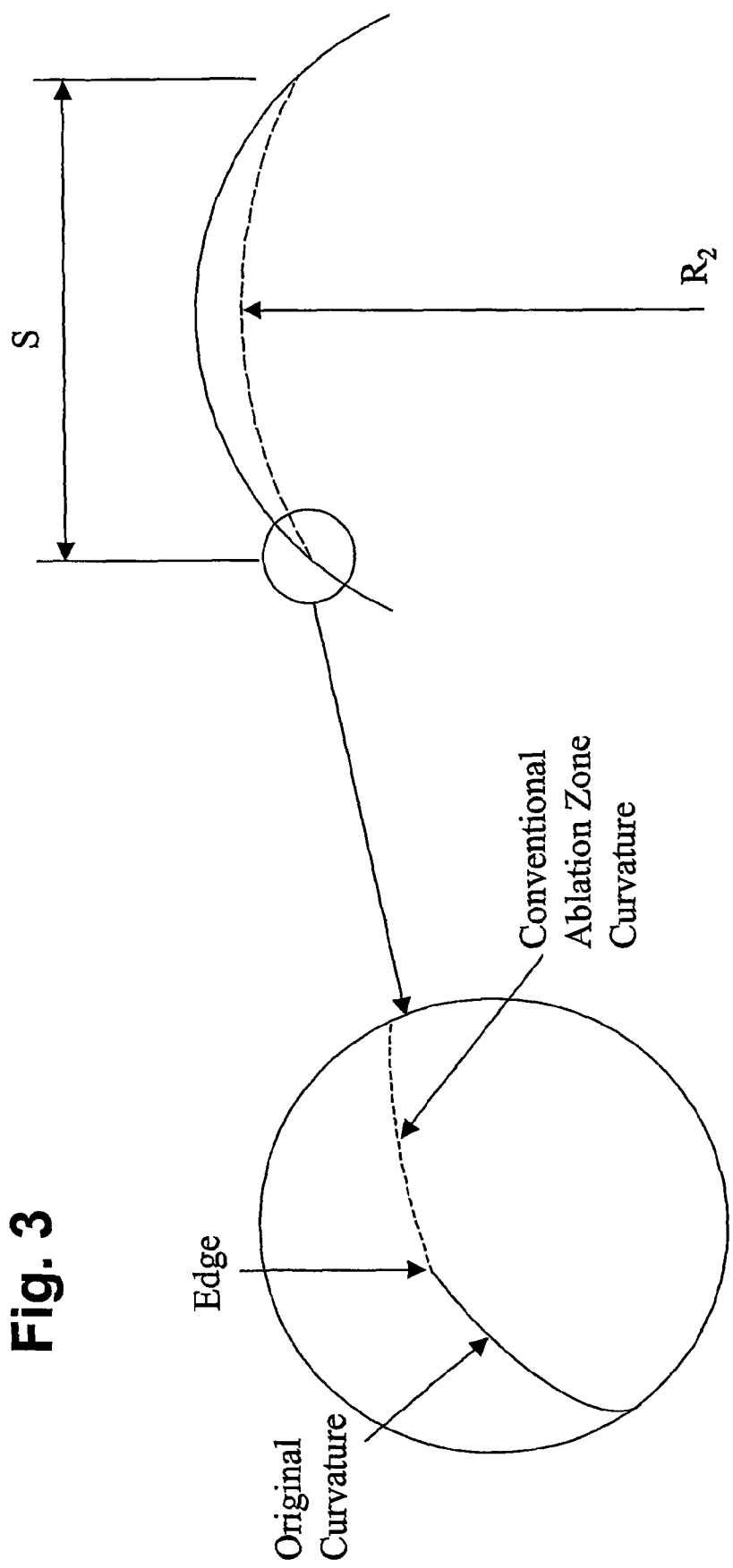
FIG. 3 illustrates a transition between an ablated area and a non-ablated area having curvature discontinuities.
Figure 4:
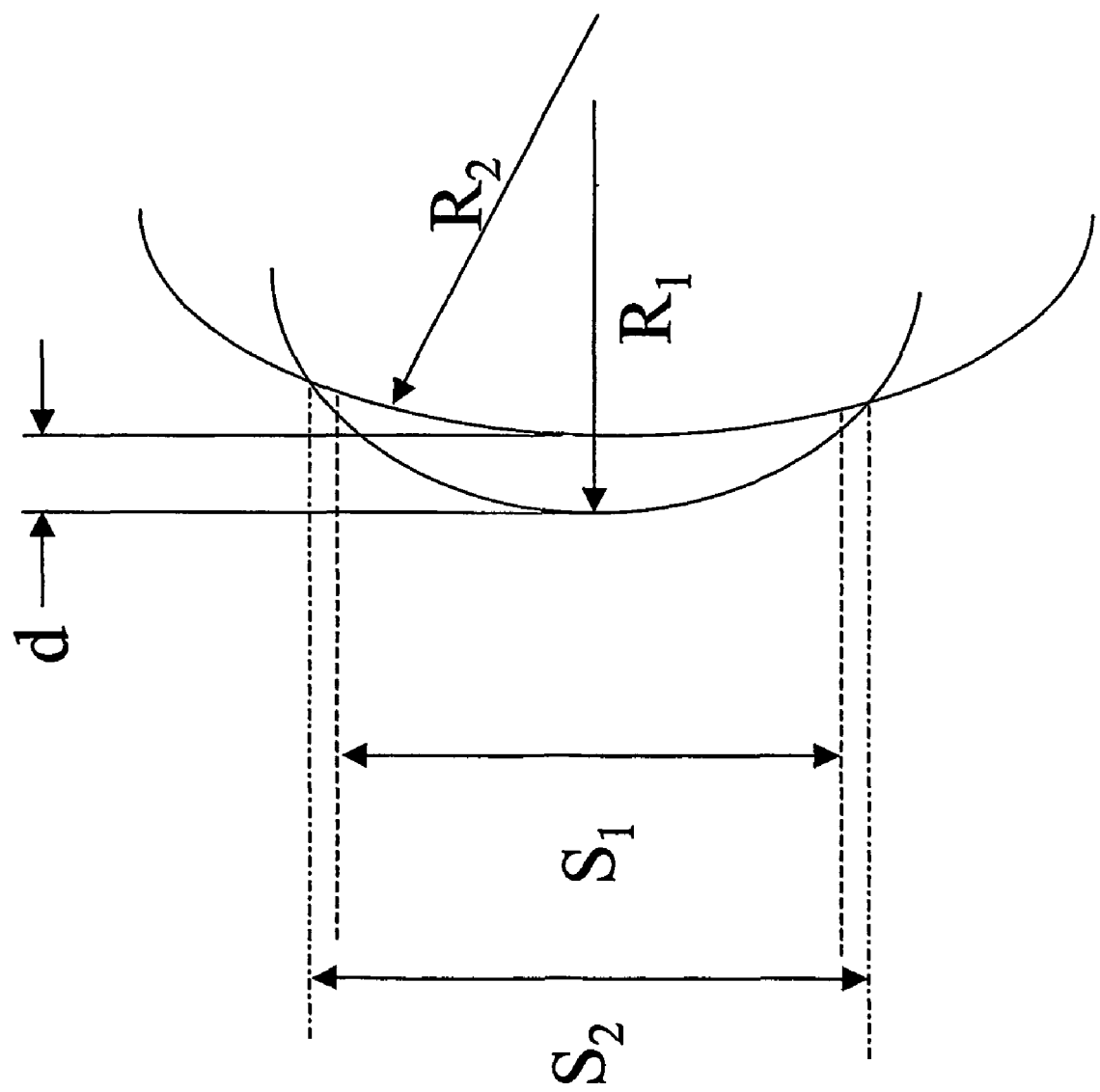
FIG. 4 illustrates a conventional transition zone between an ablated area and a non-ablated area.
Figure 5:
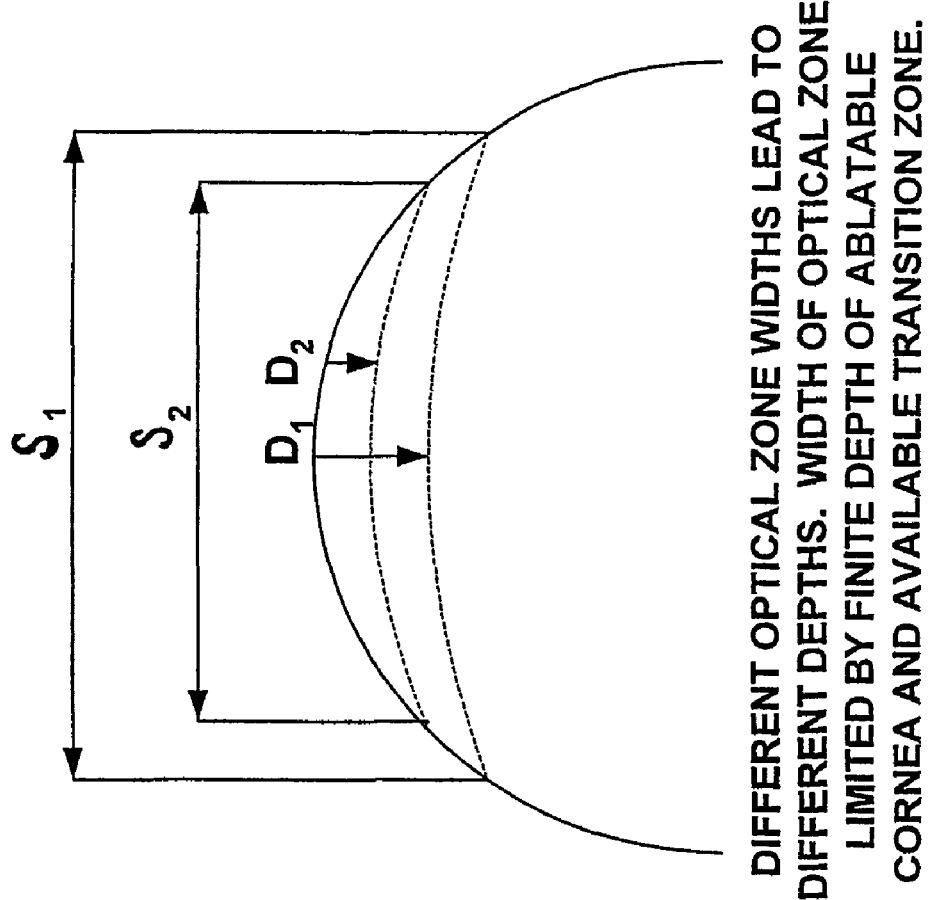
FIG. 5 illustrates two different ablation widths and the corresponding ablation depths.

Skilled artisans appreciate that elements in the figures are illustrated for simplicity and clarity and have not necessarily been drawn to scale. For example, the dimensions of some of the elements in the figures may be exaggerated relative to other elements to help to improve understanding of embodiment(s) of the present invention.

The corneal ablative pattern described herein provides a wider ablation zone that includes both an optical zone and a transition zone, where the transition zone has a continuous curvature and its effects on vision correction are accounted for in the pattern design. It is to be appreciated that post-ablative corneal shape, and thus visual performance, is the function of at least three factors: the ablation profile, the healing process, and the biomechanical response of the cornea to structural change. Furthermore, there are only certain shapes a cornea will biomechanically assume. These shapes depend, at least in part, on epithelial thickness, stromal thickness and response to severing stroma and/or lamellae. For example, the deeper the ablation in the edge of the ablation zone in a myopic procedure to generate a potentially desirable post-operative prolate shape, the greater the number of severed lamellae and the greater the biomechanical central flattening response to counter the effect. The transition zone of the present invention considers such factors.

LASIK, LASEK, and/or PRK procedures can be improved by taking pre-operative measurements of the eye, predicting the cornea's biomechanical response to ablative treatment, and customizing an ablative pattern design. Additionally, wave-front guided procedures may also employ a transition zone that may benefit from the systems and methods described herein. Parameters considered in customizing the ablation pattern design with an improved transition zone include, but are not limited to, the location, size, shape, depth, and number of cuts and/or ablations. In addition to pre-operative measurements, real time measurements taken during the initial steps of a surgical procedure facilitate analyzing individualized responses and thus in designing a combined ablation zone that includes both an optical zone and an improved transition zone of continuous curvature, and which considers and accounts for the corrective effects of the conventional transition zone. For example, comparison of data including, but not limited to, pre-flap, post-flap, pre-ablation and post-ablation data like corneal thickness, flap thickness, corneal topography, and wave-front data provide predictive information applicable to modifying an ablation pattern design.

As used herein, the term "biomechanical response" means a mechanical or physical response to a perturbation or other stimulus (e.g., cutting the cornea, ablating the cornea).

As used in this application, the term "computer component" refers to computer-related entities such as hardware, firmware, software, a combination thereof, or software in execution. For example, a computer component can be, but is not limited to being, a process running on a processor, a processor, an object, an executable, a thread of execution, a program and a computer. By way of illustration, both an application running on a server and the server can be computer components. One or more computer components can reside within a process and/or thread of execution and a computer component can be localized on one computer and/or distributed between two or more computers.

"Signal", as used herein, includes but is not limited to one or more electrical or optical signals, analog or digital, one or more computer instructions, a bit or bit stream, or the like.

"Software", as used herein, includes but is not limited to, one or more computer readable and/or executable instructions that cause a computer or other electronic device to perform functions, actions and/or behave in a desired manner. The instructions may be embodied in various forms like routines, algorithms, modules, methods, threads, and/or programs. Software may also be implemented in a variety of executable and/or loadable forms including, but not limited to, a stand-alone program, a function call (local and/or remote), a servelet, an applet, instructions stored in a memory, part of an operating system or browser, and the like. It is to be appreciated that the computer readable and/or executable instructions can be located in one computer component and/or distributed between two or more communicating, co-operating, and/or parallel processing computer components and thus can be loaded and/or executed in serial, parallel, massively parallel and other manners.

In a myopic procedure, inside the ablation zone, thickness decreases as predicted by the shape subtraction model. However, outside the ablation zone, thickness unexpectedly increases. In addition, regression analysis between the central and peripheral curvature changes shows a negative correlation ($p<0.0053$), indicating that greater central flattening produces greater peripheral steepening. Elevation and pachymetry maps also show peripheral increases in both elevation and pachymetry outside the ablation zone, corresponding to the increase in curvature. Once again, the shape subtraction model is found lacking, and thus ablative design patterns based on the shape subtraction model can be improved by considering individual biomechanical response to corneal structural changes and contribution of areas outside the optical zone to central vision.

Altering the corneal structure alters the shape of the entire cornea, whether using an incisional, ablative or thermal mechanism. Fundamentally, if the cornea were a piece of plastic, radial keratotomy would not work. Yet, in laser refractive surgery, the structural link between the central and peripheral cornea has not been employed to design ablation patterns. Thus, this application describes systems and methods that consider peripheral stromal thickening or an increase in the corneal elevation outside the optical and/or ablation zone when designing an ablation pattern. Regression analysis between central curvature change and peripheral elevation change from thirty subjects who underwent LASIK procedures demonstrated a positive correlation ($R2=0.56$, $p<0.0001$) indicating that the greater the increase in elevation outside the ablation zone, the greater the flattening curvature change centrally.

In one case study, regression analysis of central curvature versus peripheral stromal thickness was performed. Central curvature has a negative correlation with peripheral thickness, both inferior and superior, meaning the greater the peripheral thickness, the flatter the central curvature. Thus, the application describes example systems and methods that design ablation patterns with improved transitional zones with continuous curvature based, at least in part, on peripheral stromal thickness.

Figure 6:
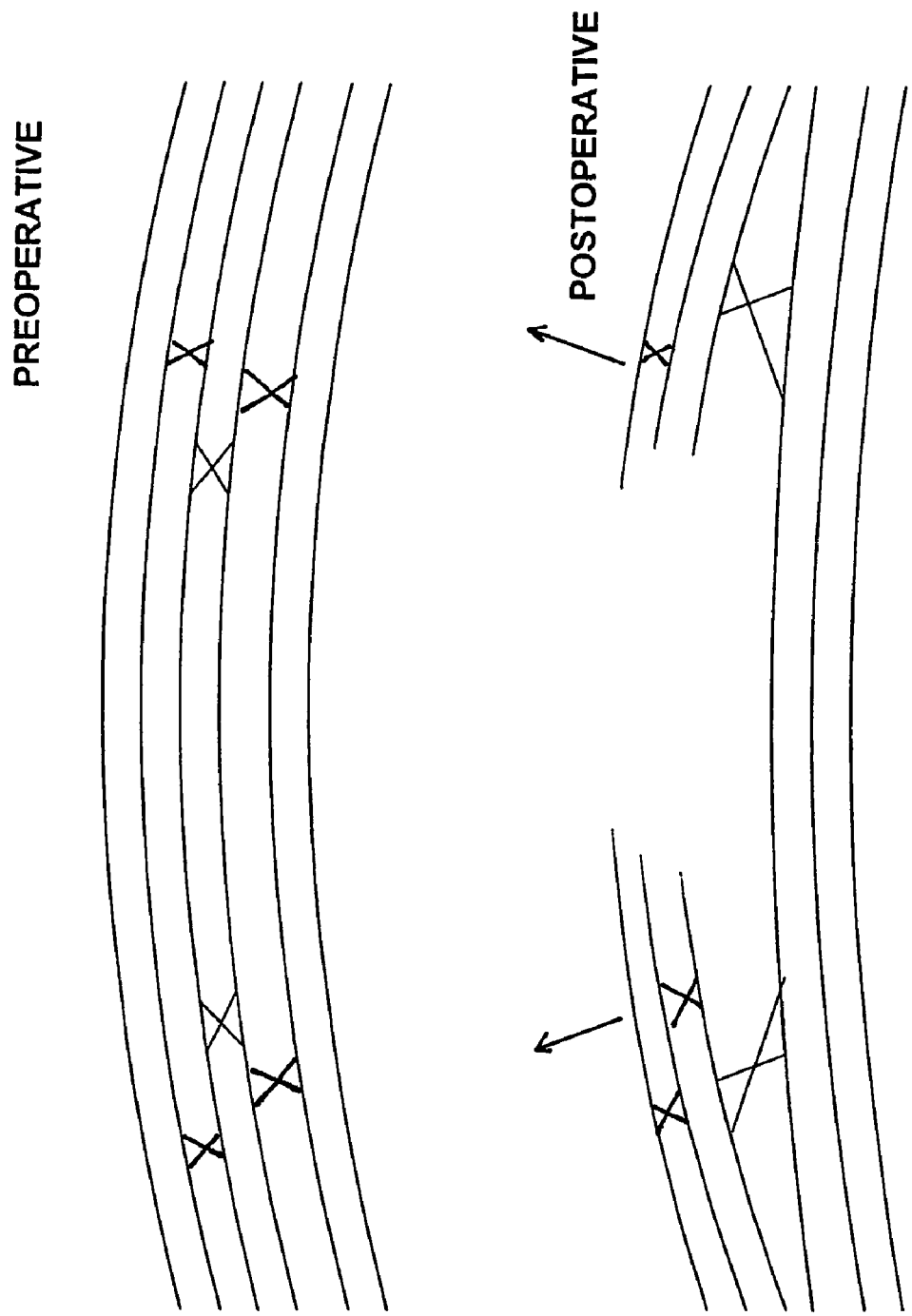
FIG. 6 illustrates a conceptual model for predicting biomechanical central flattening due to severing corneal lamellae.

An example model is presented in FIG. 6 that predicts biomechanical central corneal flattening as a direct consequence of severed corneal lamellae. Rather than modeled like a piece of plastic as with prior method, the cornea in the present invention is modeled as a series of stacked rubber bands (lamellae) with sponges between each layer (interlamellaer spaces filled with ground substance or matrix). The lamellae carry a tensile load since there is a force pushing on them from underneath (intraocular pressure) and the ends are held tightly by the limbus. The amount of water that each matrix can hold is determined by how tightly the lamellae are pulled. As the lamellae are pulled more tightly, tension increases and water is squeezed out of the interleaving matrix resulting in smaller, interlamellaer spacing. This is analogous to the pre-operative condition illustrated in FIG. 6.

After myopic laser refractive surgery, a series of lamellae are severed circumferentially and removed centrally as shown in FIG. 6. The remaining peripheral lamellae segments relax just as tight rubber bands would relax once cut. With the reduction of tension in the lamellae, the squeezing force on the matrix is reduced and the distance between lamellae expands due to negative intrastromal fluid pressure. This is analogous to the sponges taking up water if the rubber bands are cut. This allows the periphery of the cornea to thicken. Due to cross linking between the lamellae layers, the expansion force pulls on the underlying intact lamellae as indicated by the arrows pointing radially outward. An outward force in the periphery pulls laterally on the center and flattens it. Thus, the cornea will flatten centrally with procedures that circumferentially sever lamellae, including hyperopic procedures and therapeutic procedures.

Figure 7:
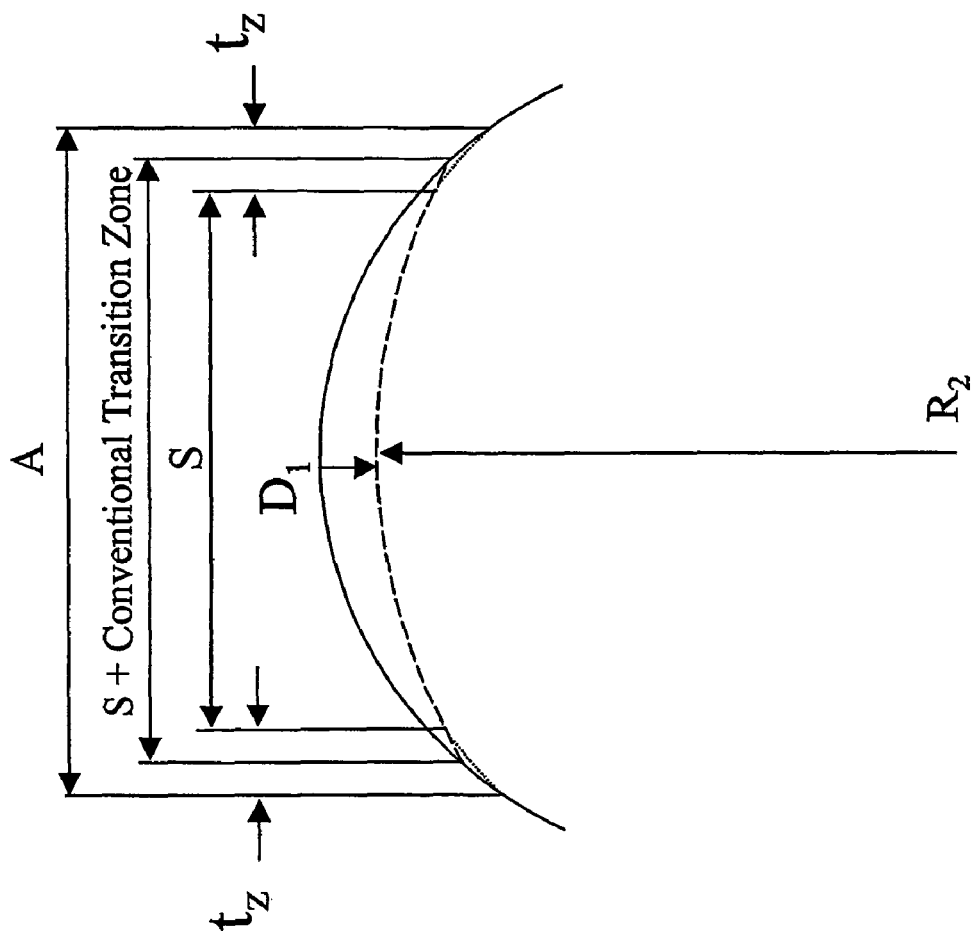
FIG. 7 illustrates a conceptual model of an ablation pattern comprising a customized transition zone modifying a programmed optical zone correction according to the present invention.

The biomechanical flattening enhances a myopic procedure, works against a hyperopic procedure, and causes flattening in a non-refractive PTK. This includes myopic profiles, hyperopic profiles, constant depth PTK profiles, as well as the simple cutting of a LASIK flap. Thus, the example systems and methods described herein rely on the assumption of central corneal flattening and peripheral steepening associated with severing lamellae. FIG. 7 is an illustration of a customized transition zone calculated according to methodology of the present invention. As shown in this illustrated example, the transition zone $t_z$ modifies the ablation pattern A starting at the programmed optical zone S to eliminate curvature discontinuities at the edge of optical zone S. It is to be appreciated that a transition zone $t_z$ based at least on the pre-operative data could also conceivable start at the edge or inside of the programmed optical zone S. It is to be appreciated that by expanding the ablation pattern A and widening and/or deepening the transition zone $t_z$ (i.e., the programmed optical zone correction depth), corneal crosslinks, which are preferentially distributed anteriorly and peripherally, are removed. Computational modeling indicates that applying such a transition zone pattern reduces the biomechanical response of the cornea and allows a more optimal corneal shape to be achieved.

In example models employed by the systems and methods described herein, the stroma, which makes up about 90% of the total corneal thickness, most significantly influences the mechanical response of the cornea to perturbation (e.g., cutting, ablation). The stroma is approximately 78% water by weight, 15% collagen, and 7% other proteins, proteoglycans, and salts. Three hundred to five hundred lamellae, flattened bundles of parallel collagen fibrils, run from limbus to limbus without interruption. In the posterior two thirds of the stroma, the lamellae are successively stacked parallel to the corneal surface so that each lamellae has an angular offset from its anterior and posterior neighbors. Anteriorly, the lamellae are more randomly oriented, often obliquely to the corneal surface, are more branched, and are significantly interwoven. Accounting for the biomechanical response of lamellar severing in the expanded transition zone facilitates improving resulting vision.

The systems and methods described herein assume that shape changes measured outside an optical zone and/or ablation zone can affect curvature changes within an optical and/or ablation zone. Central curvature change in refractive surgery is not solely a product of the optical zone design pattern. When peripheral thickness and ablation zone bias are included in a regression model, over 83% of the variance and curvature response is explained by peripheral thickening. Thus, a biomechanical response considered herein assumes additional flattening over and above conventionally programmed ablation profiles. This occurs in myopic (with an intent to flatten), hyperopic (with an attempt to steepen), and/or non-refractive PTK.

In LASIK surgery, cutting the flap alters the corneal structure. Following the cutting of the corneal flap, corneal measurements taken are therefore employed by example methods and systems described herein. The microkeratomic incision for the flap produces changes in the cornea. The redistribution of strain caused by the keratomic incision causes the central cornea to flatten and the peripheral stroma matrix to thicken and become steeper. Such reshaping assists with a central myopic correction, where decreased corneal curvature is prescribed, and works against a hyperopic correction where increased corneal curvature is prescribed. Since cutting the LASIK flap produces a biomechanical response, a method for customizing a refractive ophthalmic treatment by designing the ablation pattern with an improved optical zone plus transitional zone can include pre-operatively measuring the cornea, cutting the flap, measuring the cornea and/or the flap, calculating a customized transition zone for a designed ablation pattern, and performing an ablation based on the pattern.

In LASEK and PRK surgery, no flap is cut. However, based on pre-operative measurements, with reference to a biomechanical response model, an ablation pattern with an improved optical zone plus transition zone is similarly provided.

In an example method, corneal measurements are taken by methods including, but not limited to, corneal topography, optical coherence tomography, ultrasound, refraction, and/or wave-front analysis. In LASIK, these measurements are taken before and after the microkeratomic incision for the corneal flap. In LASEK and PRK, the measurements are only taken before the procedure. In LASIK, differences in corneal measurements are compared to expected and achieved post-cut results. Comparison of the measurements before and after the incision facilitate adjusting an ablative pattern design to account for the measured biomechanical response due to the cutting, and the predicted biomechanical response anticipated through the ablation. Ablation pattern adjustments can thus be made in advance of the ablation in a separate procedure and/or in real time as an intraoperative adjustment after the perturbation (e.g., cut, ablation) but before the ablation.

Optimal surgical procedures benefit from considering the biomechanical results of the ablative procedure itself. Thus, an example LASIK surgical technique employing the systems and methods described herein includes, but is not limited to, accessing a model of predicted responses based on empirical data collected from corneas before and after cutting a flap, ablation, and healing. The technique further includes taking pre-perturbation measurements (e.g., thickness profile, curvature profile, corneal size) and employing these measurements in connection with the model to facilitate computing ablation pattern designs. The method further includes taking post perturbation measurements (e.g., thickness profile, curvature profile, central flattening, peripheral thickening), and employing these measurements to compute one or more ablation parameters. A sample LASEK or PRK surgical technique would only acquire pre-operative data that can be employed to query the biomechanical response model. The technique further includes comparing the differences between the pre-perturbation measurements and the post perturbation measurements to facilitate refining the computed ablation parameters and/or the model.

Example biomechanical response models can also consider Young's modulus measurements, and other factors including, but not limited to, age, sex, race, years of contact lens wear, thickness, curvature, and corneal size. While data concerning some factors are acquired by measuring, other data can be acquired during a patient interview e.g., years of contact lens use). Measurements of one or more of these factors facilitate selecting which pre-operative parameters to employ to predict a biomechanical response. Thus, ablation patterns may be designed based on pre-operative data.

Pre-operative and postoperative measurements can be input to one or more computer components by methods including, but not limited to, key stroke, direct data transfer, and so on. During cornea surgery, the methods described herein may be performed on a computer system with which a surgical team member communicates. Data may be input to the computer during the surgical process. The method can then produce data, such as ablation parameters, that can be employed in subsequent steps of the surgery.

Figure 8:
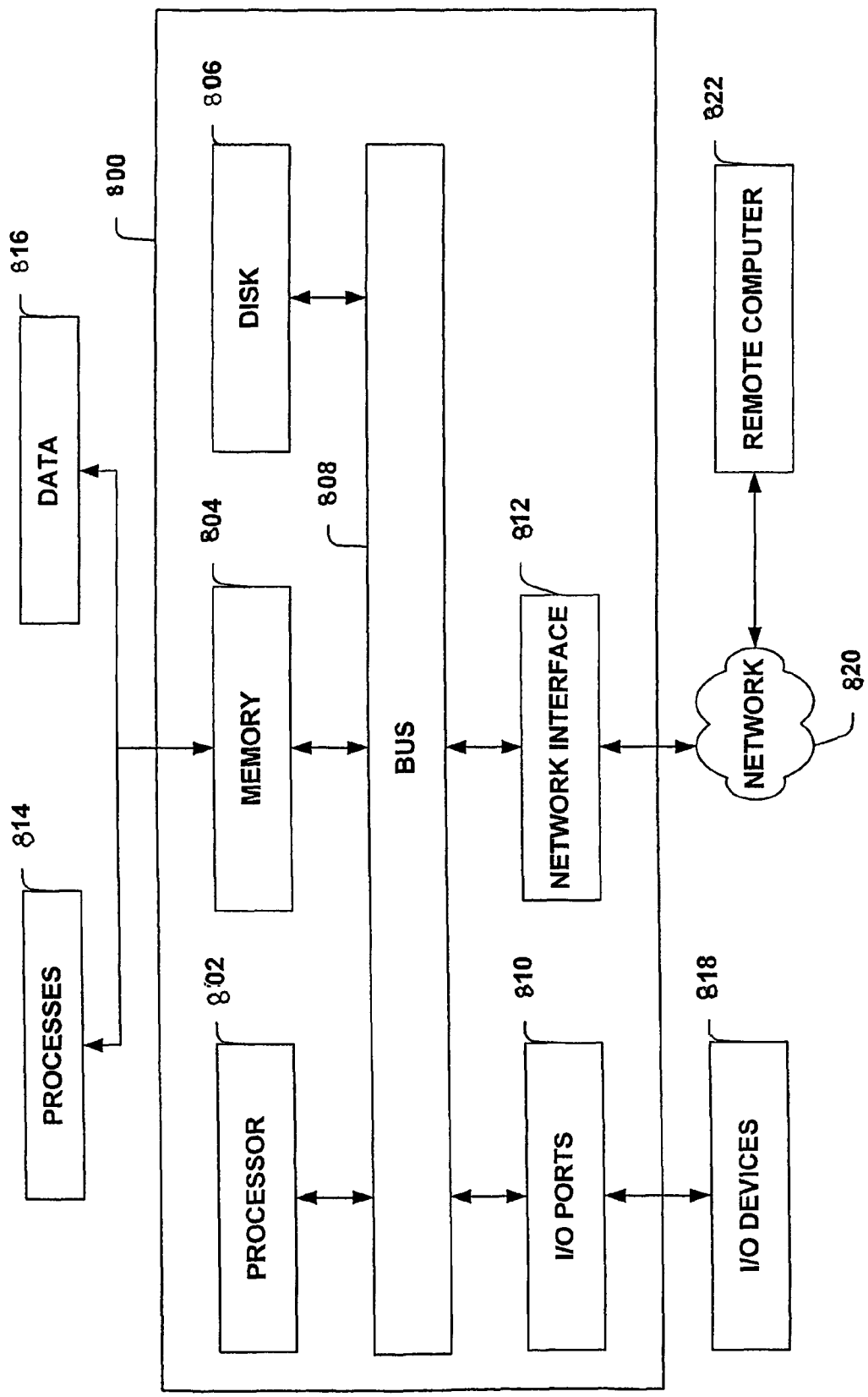
FIG. 8 is a schematic block diagram of an illustrative computing environment that supports the methods and systems described herein.

Those skilled in the art of computer programming, mathematical computer modeling, and/or data base manipulation and administration will readily appreciate that example systems and methods described herein may be embodied in software and/or one or more computer components. For example, FIG. 8 illustrates a computer 800 that includes a processor 802, a memory 804, a disk 806, input/output ports 810, and a network interface 812 operably connected by a bus 808. Executable components of systems described herein may be located on a computer like computer 800. Similarly, computer executable methods described herein may be performed on a computer like computer 800. It is to be appreciated that other computers may also be employed with the systems and methods described herein. The processor 802 can be a variety of various processors including dual microprocessor and other multi-processor architectures.

The memory 804 can include volatile memory and/or non-volatile memory. The non-volatile memory can include, but is not limited to, read only memory (ROM), programmable read only memory (PROM), electrically programmable read only memory (EPROM), electrically erasable programmable read only memory (EEPROM), and the like. Volatile memory can include, for example, random access memory (RAM), synchronous RAM (SRAM), dynamic RAM (DRAM), synchronous DRAM (SDRAM), double data rate SDRAM (DDR SDRAM), and direct RAM bus RAM (DRRAM). The disk 806 can include, but is not limited to, devices like a magnetic disk drive, a floppy disk drive, a tape drive, a Zip drive, a flash memory card, and/or a memory stick. Furthermore, the disk 806 can include optical drives like, compact disk ROM (CD-ROM), a CD recordable drive (CD-R drive), a CD rewriteable drive (CD-RW drive) and/or a digital versatile ROM drive (DVD ROM). The memory 804 can store processes 814 and/or data 816, for example. The disk 806 and/or memory 804 can store an operating system that controls and allocates resources of the computer 800.

The bus 808 can be a single internal bus interconnect architecture and/or other bus architectures. The bus 808 can be of a variety of types including, but not limited to, a memory bus or memory controller, a peripheral bus or external bus, and/or a local bus. The local bus can be of varieties including, but not limited to, an industrial standard architecture (ISA) bus, a microchannel architecture (MSA) bus, an extended ISA (EISA) bus, a peripheral component interconnect (PCI) bus, a universal serial (USB) bus, and a small computer systems interface (SCSI) bus.

The computer 800 interacts with input/output devices 818 via input/output ports 810. Input/output devices 818 can include, but are not limited to, a keyboard, a microphone, a pointing and selection device, cameras, video cards, displays, and the like. The input/output ports 810 can include but are not limited to, serial ports, parallel ports, and USB ports.

The computer 800 can operate in a network environment and thus is connected to a network 820 by a network interface 812. Through the network 820, the computer 800 may be logically connected to a remote computer 822. The network 820 includes, but is not limited to, local area networks (LAN), wide area networks (WAN), and other networks. The network interface 812 can connect to local area network technologies including, but not limited to, fiber distributed data interface (FDDI), copper distributed data interface (CDDI), ethernet/IEEE 802.3, token ring/IEEE 802.5, and the like. Similarly, the network interface 812 can connect to wide area network technologies including, but not limited to, point to point links, and circuit switching networks like integrated services digital networks (ISDN), packet switching networks, and digital subscriber lines (DSL).

Figure 9:
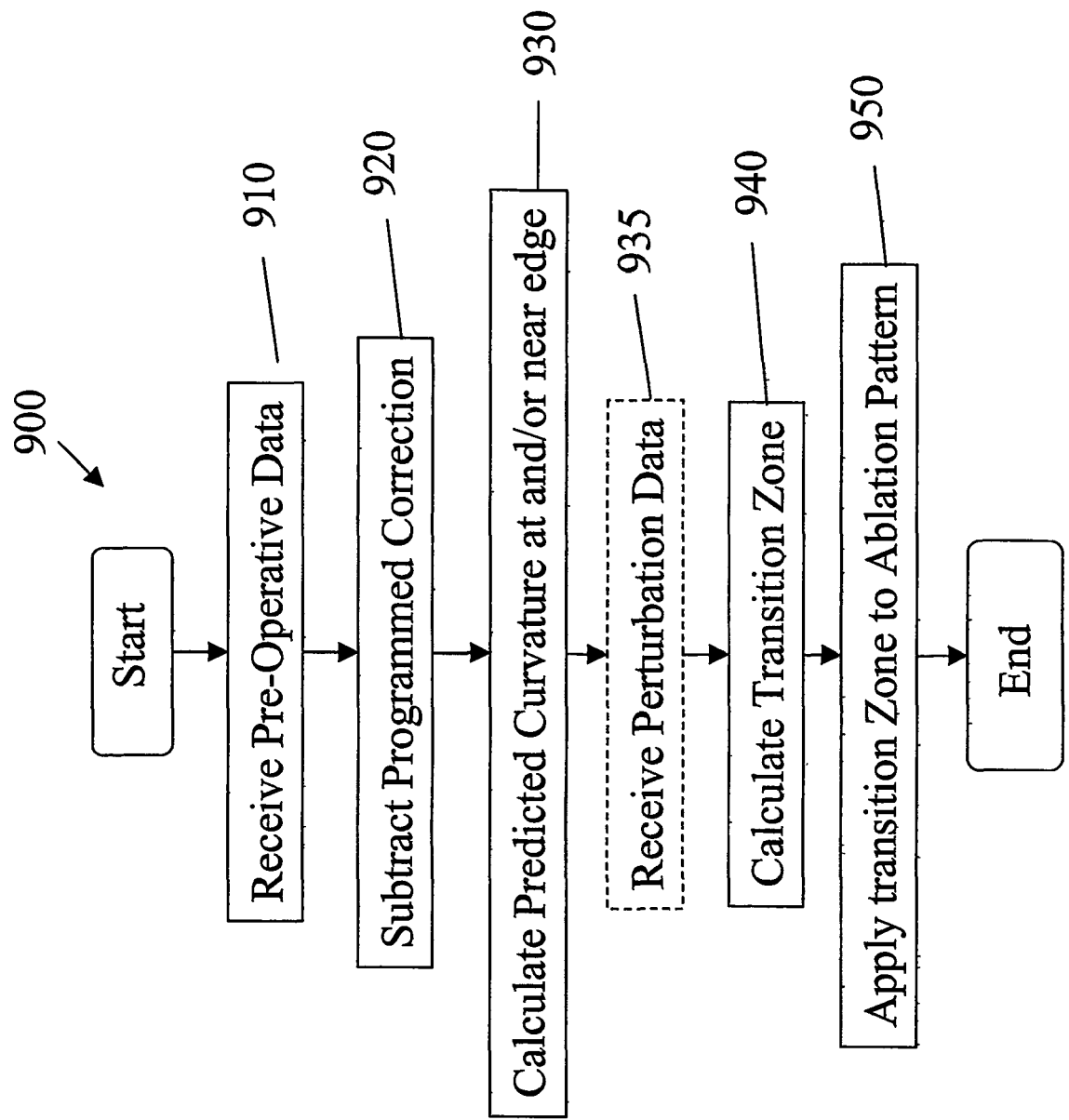
FIG. 9 is a flow chart of an example method for designing a customized transition zone pattern.
Figure 10:
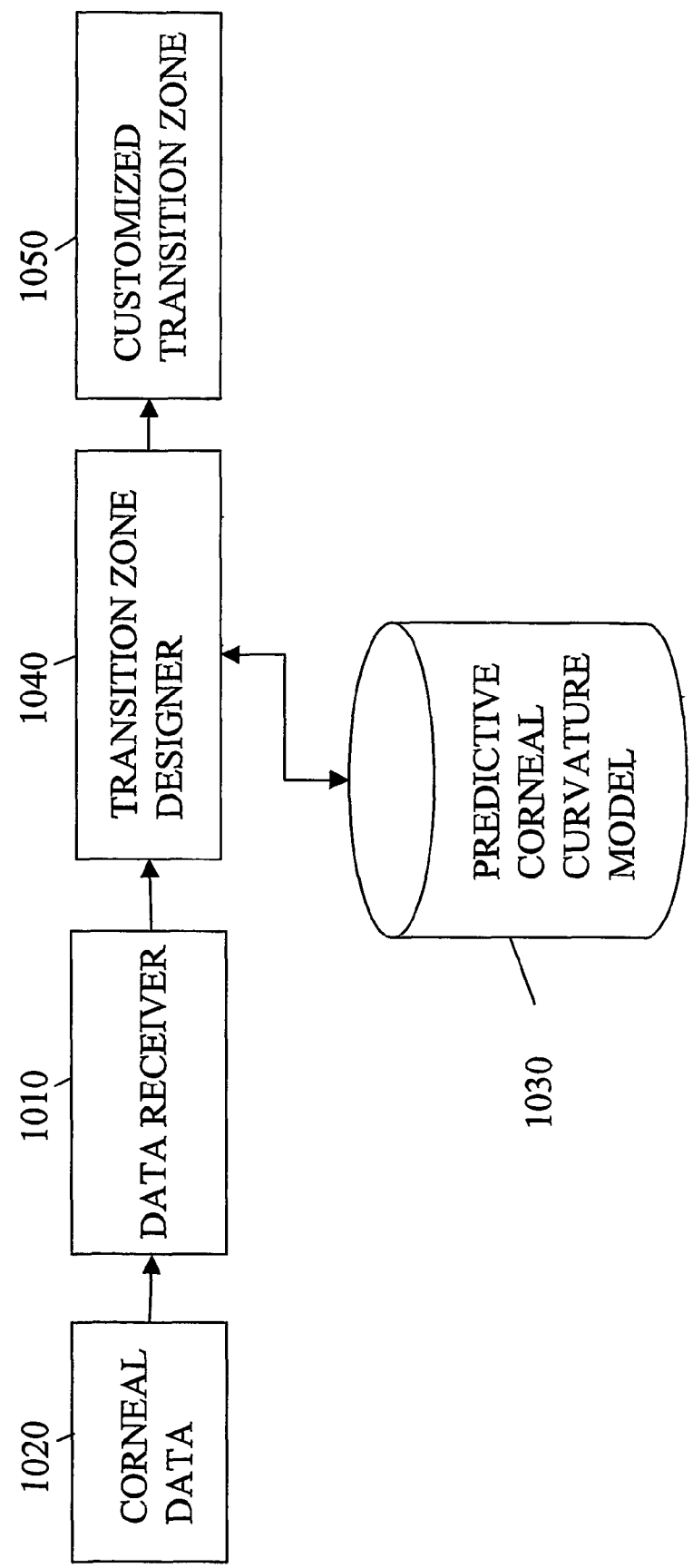
FIG. 10 is a schematic block diagram of an example system for designing a customized transition zone pattern.

In view of the exemplary systems shown and described herein, example methodologies that are implemented will be better appreciated with reference to the flow diagram of FIGS. 9 and 10. While for purposes of simplicity of explanation, the illustrated methodologies are shown and described as a series of blocks, it is to be appreciated that the methodologies are not limited by the order of the blocks, as some blocks can occur in different orders and/or concurrently with other blocks from that shown and described. Moreover, less than all the illustrated blocks may be required to implement an example methodology. Furthermore, additional and/or alternative methodologies can employ additional, not illustrated blocks. In one example, methodologies are implemented as computer executable instructions and/or operations, stored on computer readable media. The computer readable media includes, but is not limited to, an application specific integrated circuit (ASIC), a compact disc (CD), a digital versatile disk (DVD), a random access memory (RAM), a read only memory (ROM), a programmable read only memory (PROM), an electronically erasable programmable read only memory (EEPROM), a disk, a carrier wave, and a memory stick.

In the flow diagrams, rectangular blocks denote "processing blocks" that may be implemented, for example, in software. Similarly, the diamond-shaped blocks denote "decision blocks" or "flow control blocks" that may also be implemented, for example, in software. Alternatively, and/or additionally, the processing and decision blocks can be implemented in functionally equivalent circuits like a digital signal processor (DSP), an application specific integrated circuit (ASIC), and the like.

A flow diagram does not depict syntax for any particular programming language, methodology, or style (e.g., procedural, object-oriented). Rather, a flow diagram illustrates functional information one skilled in the art may employ to program software, design circuits, and so on. It is to be appreciated that in some examples, program elements like temporary variables, routine loops, and so on are not shown.

Turning now to FIG. 9, a flow chart illustrates an example method 900 that facilitates an increased functional optical zone with a customized transition zone pattern of continuous curvature, where the corrective properties of the transition zone are included in the ablation zone pattern design. At 910, the method 900 receives pre-operative data concerning a cornea on which a refractive ophthalmic treatment will be performed. The pre-operative data in part is used to determine a programmed optical zone correction used in the ablation zone pattern. The pre-operative data can include, but is not limited to, topographic data, pachymetric data, elevation data, corneal thickness data, corneal curvature data, wave-front data, and intraocular pressure data, where such data are associated with the cornea before it has been perturbed. The perturbation can be one of a corneal incision, a corneal ablation, a LASIK flap cut, ultrasonic measurements, and peeling the epithelial layer from the cornea, for example. It is to be appreciated that the ablation zone pattern comprises the programmed optical zone correction (pattern) and the customized transition pattern derived from the methodology of the present invention.

At 920, the method 900 subtracts the programmed optical zone correction from corneal measurements provided in the pre-operative data to provide location of the programmed optical zone edge. At 930, the method 900 calculates the predicted curvature at and/or near the edge of the optical zone after application of the programmed optical zone correction. Optionally, at 935, the method 900 may receive post-perturbation data that can be used to correlate and/or recalculated the predicted curvature at and/or near edge of the optical zone for further refinement.

At 940, based, at least in part, on the pre-operative data received at 910 and the predicted curvature at the edge calculated at 930, the method 900 then calculates a customized transition zone pattern which addresses curvature discontinuity by eliminating its occurrence in and/or near the programmed optical zone. In particular, with the predicated curvature at and/or near the edge of the optical zone calculated at 930, the method 900 uses a curve fitting algorithm which generates a transition zone with a continuous second derivative along the profile of the cornea outwardly from the programmed optical zone correction. It is to be appreciated that any conventional curve fitting algorithm, such as spline fitting, arc-step fitting, least-squares fitting, non-linear least squares fitting may be used by the present invention.

At 950, the method 950 applies the calculated transition zone to a designed ablation pattern. The ablation pattern may be designed in accordance with a biomechanical response modeled in a biomechanical response model, such as discussed in co-pending application entitled Parametric Model Based Ablative Surgical System and Methods, Ser. No. 60/433,739, commonly assigned to The Ohio State University, which the teachings of which is herein incorporated fully be reference. In one example, the biomechanical response model predicts the biomechanical response, at least in part, by considering the impact of severing corneal lamellae during the perturbation.

In an extension of method 900 (not illustrated), additional processing may be undertaken. This additional processing includes receiving post perturbation data, which can include, but is not limited to, topographic data, pachymetric data, elevation data, total corneal thickness data, corneal curvature data, wave-front data, flap thickness data, and intraocular pressure data. The perturbation can be, for example, a corneal incision, a corneal ablation, a LASIK flap cut, and an epithelial layer peel. The additional processing can also include receiving post-operative diagnosis data and selectively updating the biomechanical response model based, at least in part, on the post-perturbation data and/or the post-operative diagnosis data. In this way, a predictive biomechanical response model can be updated over time to become more complete and thus provide predictions that are even more accurate and thus better designs. The post-operative diagnosis data can include, but is not limited to, patient satisfaction data, patient vision data, patient halo effect data, topographic data, pachymetric data, elevation data, total corneal thickness data, corneal curvature data, wave-front data, and intraocular pressure data.

Turning now to FIG. 10, a system 1000 for calculating a customized transition zone, which addresses curvature discontinuities in a programmed optical zone correction, is illustrated. The system 1000 includes a data receiver 1010 that receives corneal data 1020. The corneal data 1020 can include, but is not limited to, topographic data, pachymetric data, elevation data, total corneal thickness data, corneal curvature data, wave-front data, and intraocular pressure data measured before and/or after a cornea is processed by at least one of a cut, an ablation, and an epithelial peel. In LASEK and PRK, the corneal data will not include post-perturbation data, with the design being based on pre-operative measurements with reference to a biomechanical response model, such for example, as discussed in co-pending application entitled Parametric Model Based Ablative Surgical System and Methods, Ser. No. 60/433,739, commonly assigned to The Ohio State University, which the teachings of which is herein incorporated fully be reference.

The system 1000 may also optionally include a predictive corneal curvature model 1030. The predictive corneal curvature model 1030 facilitates selecting a transition zone curvature based on the corneal data 1020. The system 1000 includes a transition zone designer 1040 that computes the transition zone curvature pattern 1050. The designer 1040 produces a customized transition zone pattern of continuous curvature which eliminates curvature discontinuities at or near the edge of the post-operative optical zone and whose effects on minimizing the biomechanical response can then be applied and accounted for in an ablation zone design.

Figure 11:
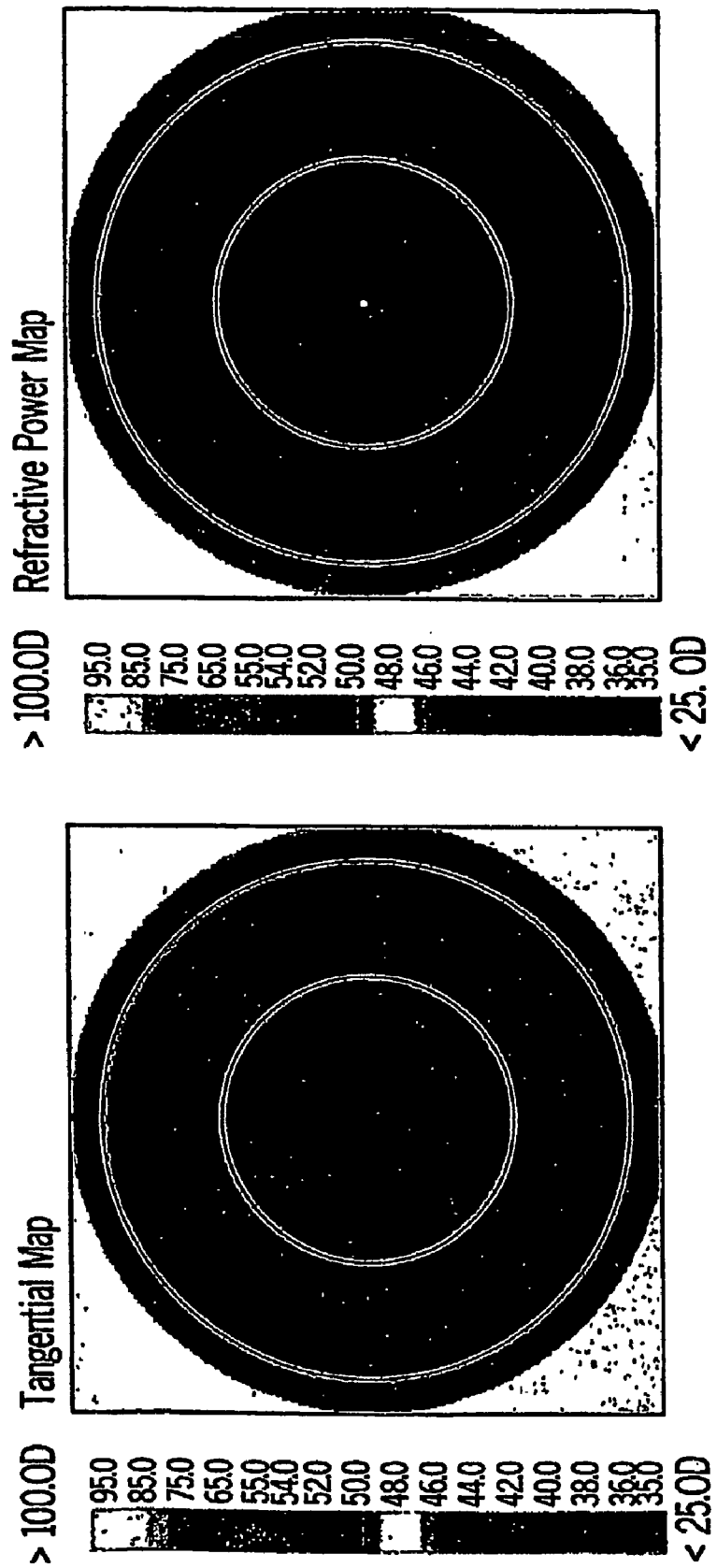
FIG. 11 illustrates a simulated tangential map and a simulated refractive power map for a cornea before ablative surgery.

Turning now to FIG. 11, a simulated tangential map and a simulated refractive power map associated with a theoretical pre-operative cornea are illustrated. On the tangential map warmer colors (e.g., yellow, red) represent more curved areas. On the refractive map, the warmer colors represent areas of greater power. Conversely, cooler colors (blue, purple) represent areas of lesser curvature on the tangential map, and lower power on the refractive map. Thus, in FIG. 11, the tangential map illustrates that the cornea is steeper in the middle and flatter in the periphery, thereby graphically illustrating a typical myopic cornea.

Figure 12:
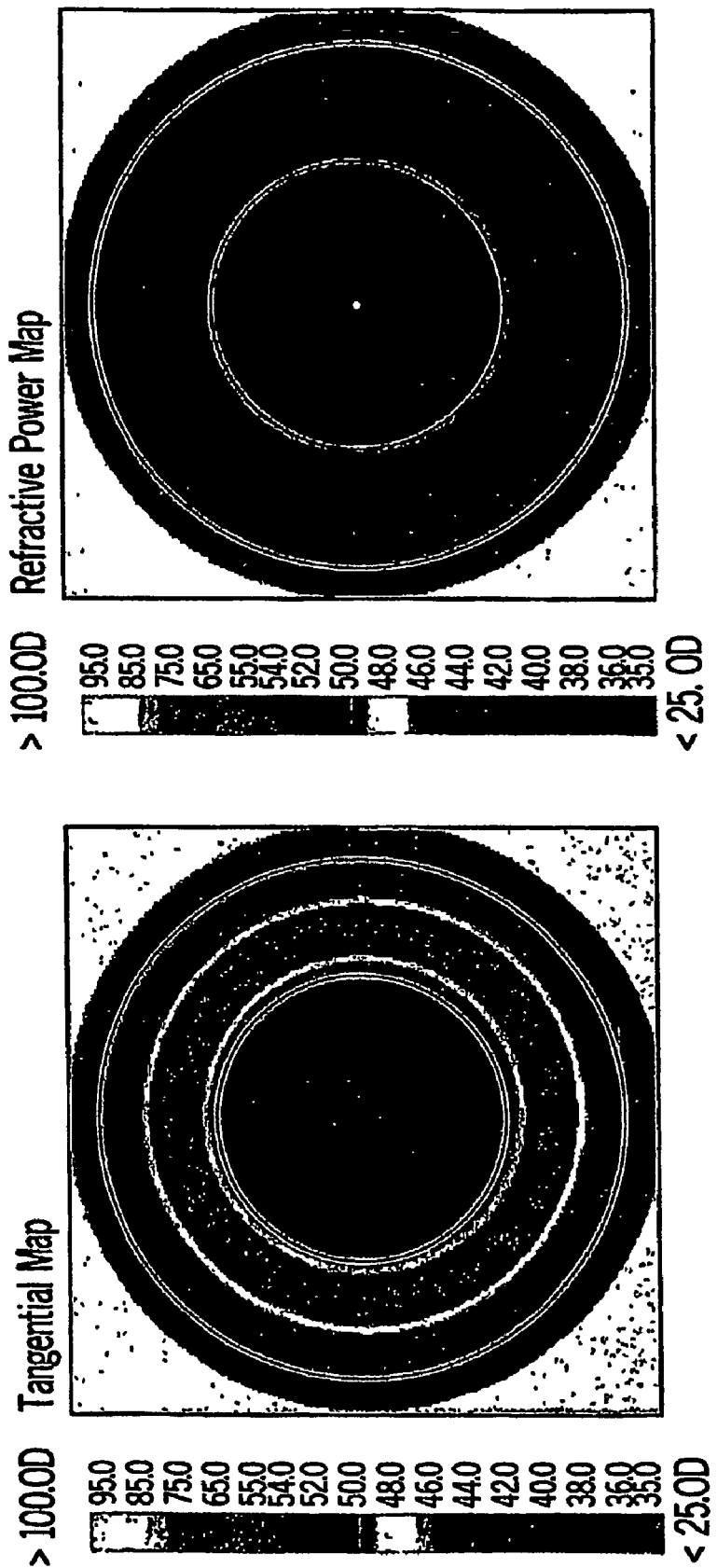
FIG. 12 illustrates a simulated tangential map and a simulated refractive power map for a cornea following a conventional ablative procedure.

FIG. 12 illustrates a simulated tangential map and a simulated refractive power map for a theoretical post-operative cornea, where the data set used represents a cornea ablated using a conventional transition zone and ablation algorithm. The tangential map illustrates a central flattening as compared to the pre-operative cornea of FIG. 11, and the characteristic red ring that indicates a very steep area caused by a sub-optimal transition zone design and peripheral biomechanical response. The refractive power map has a characteristically small central blue area that can be improved using the systems and methods described herein.

Figure 13:
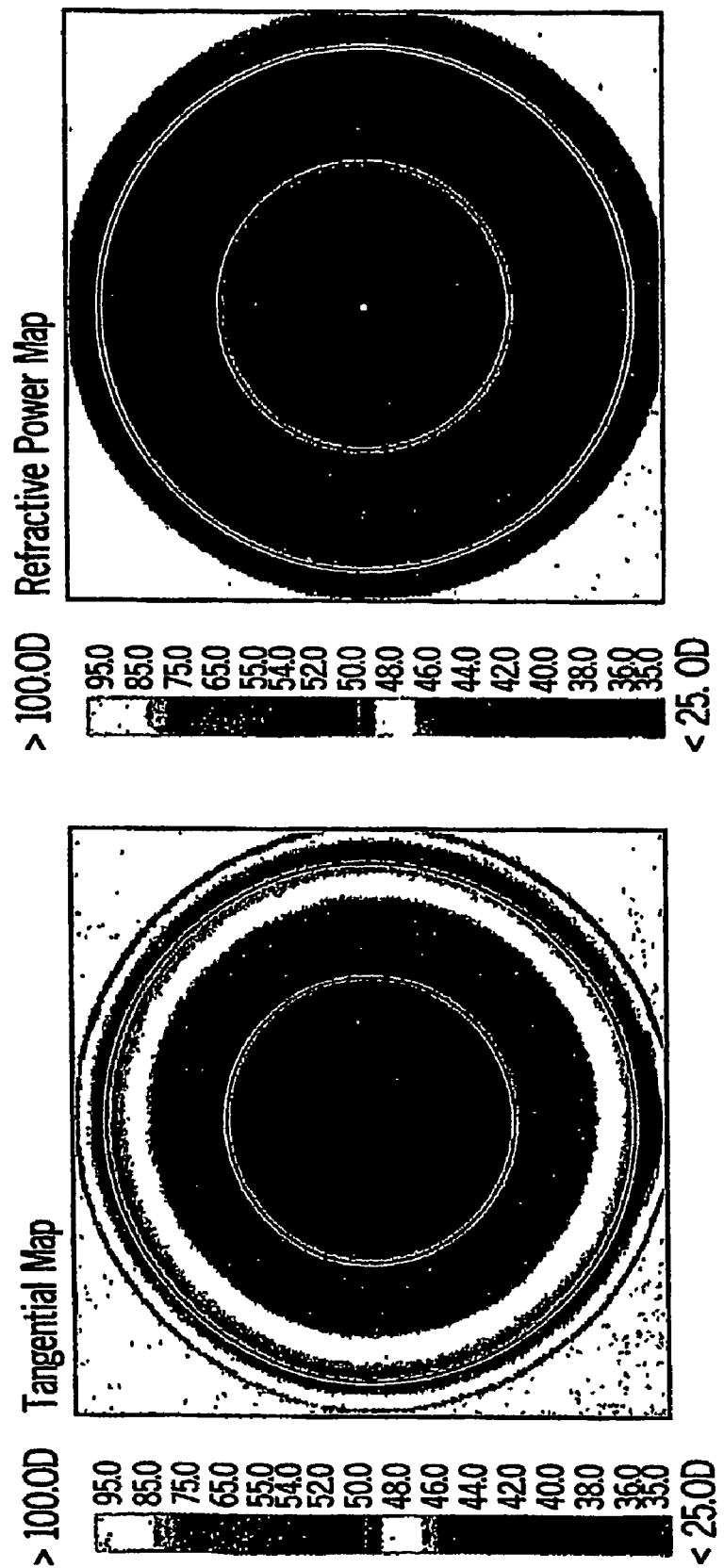
FIG. 13 illustrates a simulated tangential map and a simulated refractive power map for a cornea following an ablative procedure that employs the systems and methods described herein for an improved transition zone.

FIG. 13 illustrates a tangential map and a refractive power map for a theoretical post-operative cornea, where the data set used represents a cornea ablated using the customized transition zone described herein in an ablation pattern. In both FIGS. 12 and 13, the resulting theoretical post-operative corneas, which had substantially the same optical zone size and central flattening, applied programmed corrections based on the Munnerlyn formulae. However, unlike that of The post-operative cornea of FIG. 12, the tangential map of FIG. 13 illustrates that the red ring indicating an area of curvature discontinuities has been moved further away from the center of the cornea. This facilitates mitigating problems associated with spherical aberration. In addition, by applying the customized transition zone, a larger area of improved curvature can be achieved. For example, in the refractive power map of FIG. 13, the central blue area is much larger than that of FIG. 12, indicating a larger, more useful area of corrected vision, with fewer effects of spherical aberration.

What has been described above includes several examples. It is, of course, not possible to describe every conceivable combination of components or methodologies for purposes of describing the methods, systems, computer readable media and so on employed in improving the computation of ablation parameters. However, one of ordinary skill in the art may recognize that further combinations and permutations are possible. Accordingly, this application is intended to embrace alterations, modifications, and variations that fall within the scope of the appended claims. Furthermore, to the extent that the term "includes" is employed in the detailed description or the claims, it is intended to be inclusive in a manner similar to the term "comprising" as that term is interpreted when employed as a transitional word in a claim.

The invention claimed is:

1. A refractive ophthalmic treatment method comprising:
receiving pre-operative data concerning a cornea on which the treatment will be performed;
subtracting a programmed optical zone correction from corneal measurements provided in the pre-operative data to provide a predicted location of a post-operative optical zone edge;
calculating a predicted curvature of the cornea at the edge of the optical zone, near the edge of the optical zone, or combinations thereof after application of the programmed optical zone correction;
calculating a customized transition zone pattern which addresses curvature discontinuity by eliminating its occurrence in the programmed optical zone, near the programmed optical zone, or combinations thereof,
   wherein calculation of the customized transition zone pattern is based, at least in part, on the pre-operative data received and the predicted curvature of the cornea, and
   wherein calculation of the customized transition zone pattern involves use of a curve fitting algorithm to generate a transition zone with a continuous second derivative along a profile of the cornea outwardly from the programmed optical zone correction;
applying the customized transition zone pattern to a designed ablation zone pattern to provide an updated ablation zone pattern,
   wherein corrective properties of the customized transition zone pattern are included in the updated ablation zone pattern to facilitate an increased functional optical zone; and
performing an ablation on the cornea based on the updated ablation zone pattern.

2. The method of claim 1 wherein said pre-operative data, in part, is used to determine a programmed optical zone correction used in the ablation zone pattern.

3. The method of claim 1 wherein said pre-operative data includes, at least one of topographic data, pachymetric data, elevation data, corneal thickness data, corneal curvature data, wave-front data, and intraocular pressure data, wherein such data is associated with the cornea before and/or after a pre-operative perturbation.

4. The method of claim 3 wherein the perturbation comprises one of a corneal incision, a corneal ablation, a LASIK flap cut, an ultrasonic measurement, and peeling the epithelial layer from the cornea.

5. The method of claim 1 wherein use of a curve fitting algorithm comprises curve fitting selected from the group comprising spline fitting, arc-step fitting, least-squares fitting, and non-linear least squares fitting.

6. The method of claim 1 further comprises receiving post-perturbation data which includes, at least one of topographic data, pachymetric data, elevation data, corneal thickness data, corneal curvature data, wave-front data, and intraocular pressure data, where such data is associated with the cornea after perturbation.

7. The method of claim 6 wherein said perturbation comprises one of a corneal incision, a corneal ablation, a LASIK flap cut, an ultrasonic measurement, and peeling the epithelial layer from the cornea.

8. The method of claim 1 further comprises taking corneal measurements, which are taken by methods including, but not limited to, corneal topography, optical coherence tomography, ultrasound, refraction, and/or wave-front analysis.

* * * * *